(12) United States Patent
Lee et al.

(10) Patent No.: US 9,222,065 B2
(45) Date of Patent: Dec. 29, 2015

(54) METHOD FOR PHOTOCULTURING AND HARVESTING MICROALGAE

(71) Applicants: Tae yoon Lee, Busan (KR); Jun-Heok Lim, Busan (KR); Jea-Keun Lee, Busan (KR)

(72) Inventors: Tae yoon Lee, Busan (KR); Jun-Heok Lim, Busan (KR); Jea-Keun Lee, Busan (KR)

(73) Assignee: PUKYONG NATIONAL UNIVERSITY INDUSTRY-UNIVERSITY COOPERATION FOUNDATION, Sinseon-Ro, Nam-Gu Busn (KR)

( * ) Notice: Subject to any disclaimer, the term of this patent is extended or adjusted under 35 U.S.C. 154(b) by 224 days.

(21) Appl. No.: 14/043,690

(22) Filed: Oct. 1, 2013

(65) Prior Publication Data
US 2015/0093806 A1 Apr. 2, 2015

(51) Int. Cl.
*C12N 1/12* (2006.01)
*C12M 1/00* (2006.01)
*C12P 1/00* (2006.01)

(52) U.S. Cl.
CPC .............. *C12M 21/02* (2013.01); *C12M 29/06* (2013.01); *C12M 31/10* (2013.01); *C12M 47/02* (2013.01); *C12P 1/00* (2013.01)

(58) Field of Classification Search
CPC ...................................................... C12M 21/02
USPC ........................................... 435/257.1, 292.1
See application file for complete search history.

(56) References Cited

U.S. PATENT DOCUMENTS

| | | | |
|---|---|---|---|
| 2009/0029445 A1* | 1/2009 | Eckelberry et al. | 435/257.1 |
| 2014/0051131 A1* | 2/2014 | Dodd et al. | 435/101 |
| 2015/0090667 A1* | 4/2015 | Kneib et al. | 210/728 |

* cited by examiner

*Primary Examiner* — Nghi Nguyen
(74) *Attorney, Agent, or Firm* — John K. Park; Park Law Firm

(57) ABSTRACT

The present invention relates to a method for photoculturing and harvesting microalgae, and more particularly to a method for photoculturing and harvesting microalgae, in which a light emitting diode (LED) is used as a light source to increase the efficiency with which microalgae are cultured, and the cultured microalgae are harvested using a natural polymer flocculant and air microbubbles so that the operating cost is reduced and the range of application of microalgae is expanded, and also a semi-continuous culture method is applied so that the maximum concentration of microalgae can be produced again within a short time, even though the amount of microalgae harvested is small.

1 Claim, 1 Drawing Sheet

METHOD FOR PHOTOCULTURING AND HARVESTING MICROALGAE

CROSS-REFERENCE TO RELATED APPLICATIONS

This application claims the benefit of Korean Patent Application No.10-2013-0075606, filed on Jun. 28,2013 in the Korean Intellectual Property Office, which is incorporated herein by reference in its entirety.

BACKGROUND OF THE INVENTION

1. Field of the Invention

Examples embodiments of the present invention relate to a method for photoculturing and harvesting microalgae, in which a semi-continuous culture method that uses a reactor and a flocculation/recovery tank separate therefrom is applied, and microalgae are cultured using a light emitting diode (LED) as a light source and harvested using a natural polymer flocculant and air microbubbles.

2. Description of Related Art

Generally, the term "microalgae" refers collectively to unicellular organisms that have photosynthetic pigments and are photosynthesized. Microalgae can grow in the presence of a suitable amount of light and dissolved nutrients and can be utilized in various applications, including the production of biomass and biofuel, the improvement of atmospheric and aquatic environments, etc.

Specifically, with respect to the production of biomass by culture of microalgae and the industrial application thereof, microalgae have a characteristic in that they use sunlight as an energy source to capture carbon dioxide and produce useful substances. Studies on the production of industrially important useful substances by culture of such microalgae have been actively conducted. Generally, the term "biomass" refers to organic materials that are produced by photosynthesis. Microalgae are cultured using photosynthesis, and the biomass and industrially useful substances produced by microalgae are used in various applications, including health supplement foods, feed, cosmetic products, raw materials for development of new drugs, transportation fuels and energy, etc.

Studies on the production of biofuels using microalgae have been conducted in various ways according to environmentally friendly policies worldwide. The term "biodiesel" refers to more than 95% pure fatty acid methylesters made by reaction of animal/vegetable oils with alcohols. Biodiesel has physical/chemical properties almost similar to those of diesel oil, and thus can substitute for diesel oil. Meanwhile, high-calorie lipids are required to produce diesel from microalgae. In connection with this, *Chlorella* has high biomass productivity and a high lipid content of 28-32%, even though the lipid content thereof is lower than those of *Nannochloropsis* sp. (31-68%) and *Botryococcus* sp. (29-75%). However, due to strict culture conditions, *Chlorella* is difficult to culture. In addition, *Botryococcus* sp. has the highest lipid content among microalgae known to date, but has low cell growth rate and low biomass productivity. For this reason, *Chlorella* is a strain suitable for culturing microalgae using a high-efficiency reactor, because it has advantages in that it has high growth rate and is easy to culture.

With respect to the improvement of atmospheric and aquatic environments by culture of microalgae, the worldwide average temperature rose by 0.74° C. over the past 100 years (1906 to 2005) due to carbon dioxide, the mean sea level rose by 1.8 mm annually over a period ranging from the year 1961 to the year 1993, and the atmospheric $CO_2$ concentration increased by 30% (from 290 ppm to 360 ppm over the past one century. It is expected that, in the $21^{st}$ century, the atmospheric $CO_2$ concentration will exceed 550 ppm and the average surface temperature of the earth will increase by 1.9-4.4° C. Thus, with respect to the reduction in $CO_2$ by carbon dioxide capture mechanism and *Chlorella* culture, microalgae have substantially the same photosynthesis mechanism as higher plants. However, unlike a plant group that uses atmospheric inorganic carbon as a major carbon source, aquatic microalgae can obtain $CO_2$ from dissolved inorganic carbon (DIC). For photosynthesis, microalgae have the photosynthetic enzyme RUBISCO (ribulose bisphosphate carboxylase/oxygenase), and the diffusion of inorganic carbon to this enzyme acts as an important factor that determines the photosynthesis ability. RUBISCO has both carboxylase activity and oxygenase activity, and the two activities competitively appear depending on the concentrations of $CO_2$ and $O_2$. The $CO_2$ affinity of RUBISCO is originally low, but microalgae can show a high photosynthesis rate by a mechanism that increases the intracellular $CO_2$ concentration. Migration of $CO_2$ through the various membranes of microalgal cells in this $CO_2$ concentrating mechanism (CCM) is associated with various carbonic anhydrase enzymes that catalyze the conversion of $CO_2$ to $HCO_3^-$ ($CO_2$+$H_2O \rightarrow HCO_3^- + H^+$).

Meanwhile, many studies on the production of biomass and the removal of nutrient salts from wastewater by culture of microalgae have been conducted in order to achieve two goals: free supply of the phosphorus and nitrogen required for culture of microalgae, and water purification. Thus, with respect to improving water quality by culture of microalgae, sewage in Korea has a nitrogen content lower than a carbon content, and for this reason, the efficiency with which nitrogen is removed from sewage by a conventional sewage/wastewater treatment method using microorganisms is low. In other words, if sewage is discharged to the aquatic system in a state in which nitrogen was not sufficiently removed therefrom, economic damage and ecosystem disruption can be caused by eutrophication due to nitrogen. Microaigae are microorganisms that grow by photosynthesis using carbon dioxide as a carbon source without needing to supply an organic carbon source, and thus can capture nitrogen from wastewater having a low C/N ratio. In other words, it was reported that, when algal treatment that is a method of treating nutrients contained in livestock wastewater using microalgae is linked with existing treatment facilities, there will be various synergistic effects. Also, there was a report on the development of a medium capable of enhancing the productivities of *Chlorella ovalis* and *Dunaliella parva* using treated water fermented by humus microorganisms for the purpose of recycling livestock manure that deteriorates water quality. Moreover, there was a report on the research and development of an algae culture process using *Chlorella* sp. HA-1 to remove nutrient salts such as nitrogen and phosphorus, which are discharged from livestock wastewater to cause the eutrophication of rivers. In addition, studies were conducted to examine the ability of *Chlorella Kessleri* to remove nitrogen from wastewater having a low C/N ratio and to examine whether an apparatus can remove nitrogen from wastewater using a single strain of *Chlorella*.

Meanwhile, general methods for culturing microalgae include a method employing an open culture system. In this conventional microalgae culturing method, as shown in FIG. 1, microalgae are cultured in a natural environment such as an open pond rich in nutrient sources. Such a conventional open type microalgae culturing method has advantages in that initial capital investment and operating costs are low and the system is easy to maintain and repair. However, the conventional open type microalgae culturing method entails shortcomings in that the growth of microalgae is slow because natural light that is not effectively transferred into the culture system, the growth yield of microalgae is low, the biomass of microalgae is unstable due to contamination, nutrient sources for microalgae are non-uniformly distributed, and a large installation space is required to remove a large amount of carbon dioxide. In addition, the precipitation of microalgae occurs, and in the case of a circular pond, effective agitation of the central portion is difficult, and for this reason, the effective growth of microalgae is significantly reduced, resulting in a decrease in the productivity of microalgae. At present, the open culture systems are constructed in a raceway shape, and the raceway-shaped pond comprises one channel or several channels communicating with each other, has a depth of about 0.3 m, is made of a material such as concrete or plastic, and is provided with a paddle wheel to circulate a culture medium and prevent the precipitation of microalgae. Cooling of the culture medium in the raceway pond is controlled by evaporation, and carbon dioxide that is supplied to increase the production of microalgal biomass is mostly lost into the atmosphere, and thus the raceway pond has low photosynthesis efficiency compared to a photobioreactor. In addition, the productivity of microalgae is greatly affected by contamination with other microalgae and microorganisms.

Meanwhile, a method employing a closed culture system is shown in FIG. 2. As shown therein, the closed culture system comprises a tubular photobioreactor or a flat-plate photobioreactor and has advantages in that effective sterilization is possible, the transfer of gas is easy, and the system has a simple structure, and thus can be easily installed in any place. The tubular photobioreactor is mainly made of a glass or plastic material and has various advantages, including high agitation ability, effective sterilization, easiness of gas transfer, and easiness of spatial installation. However, it has a structural disadvantage in that, as the diameter of the tube is increased for mass culture, the surface lighting area per volume is reduced. Due to this disadvantage, an effective agitation system or an artificial lighting system is required to be additionally provided, and in this case, the length of the tube is limited. A photobioreactor for high-concentration culture is required to have a high ratio of surface area to volume, and the easiest and simplest method that satisfies this requirement is a flat-plate photobioreactor. Due to this advantage, studies on the flat-plate photobioreactor have been actively conducted. In addition, in the case of an optical fiber reactor, the efficiency with which light energy is increased by irradiating light into the reactor through optical fiber, and it is possible to obtain high carbon dioxide capture efficiency compared to that in other reactors. However, there is a disadvantage in that initial capital investment is excessively high due to expensive optical fiber and facilities.

Meanwhile, in culture methods that use different growth conditions, a photoautotrophic method requires only water, light and fundamental nutrients for the maximum growth, an autotrophic method uses carbon dioxide as a carbon source without irradiating light, a heterotrophic method performs culture in a tank in an aseptic environment under a dark condition using glucose as a carbon source without irradiating light, and a mixotrophic method uses an organic carbonic acid such as acetic acid while radiating light.

In view of the foregoing, the closed culture system that is less influenced by climate is effective for use in Korea, because the differences in temperature and rainfall between days and seasons in Korea are severe. Particularly, the open culture system is not suitable for use in Korea, because it requires a large area of the site.

In the prior art related to the present invention, patent document 1 discloses a continuous photoreactor for mass production of microalgae, which uses a fluorescent lamp as a light source.

When a fluorescent lamp is used as a light source, the photoconversion efficiency is higher than that of a glow lamp (8%), but is lower than that of LED (25-30%), and for this reason, when the fluorescent lamp emits light, the surface temperature thereof approaches 110° C., and thus it cannot be placed near growing plants or a microalgae incubator. In addition, there is a shortcoming in that the light efficiency is rapidly reduced because the intensity of light is generally inversely proportional to the distance from the light source.

In addition, there are problems in that a separate cooling system is required to be provided in order to solve the above problems and in that a separate filter for removing a harmful wavelength should be provided because the fluorescent lamp does not emit light having a wavelength unnecessary for culture.

Meanwhile, most microalgae are not easy to separate from a culture medium, because they are present at low concentration in the medium and have a size of 30 µm or less and the density thereof is slightly higher than that of water. Thus, one of important problems to be solved in a process of producing useful substances by mass production of microalgae is economic harvesting. A suitable harvesting method varies depending on the kind of algae and the intended use of the useful substances to be obtained from algae and is generally performed using complex processes such as filtration, sedimentation, flotation, centrifugation, flocculation and the like.

In the prior art related to the present invention, patent document 2 is directed to a photobioreactor for high-density culture of microalgae and a method for culturing and harvesting microalgae using the same and discloses adding flocculants ($CaCl_2$ and $FeCl_3$) to a culture medium to induce flocculation after completion of the culture of microalgae, followed by harvesting of the microalgae.

The flocculation method is a method in which microalgae are harvested using chemical flocculants or bioflocculation to separate microalgae in a culture medium from the aqueous solution. The surface of microalgae is positively charged, and thus the microalgal particles are present in a state in which they are suspended in the aqueous solution. The chemical flocculants serve to neutralize the surface charge of such microalgae to reduce the repulsive power between the particles to thereby promote the bonding between the particles. However, if the chemical flocculants are used, chemicals are included in microalgae to limit the use of the harvested microalgae. In addition, the biological flocculation method has shortcomings in that it is time-consuming and requires a somewhat complex process, compared to the flocculation method that uses the chemical flocculants.

Further, patent document 3 is directed to a photobioreactor for culture of microalgae and discloses harvesting cultured microalgae using a centrifuge in order to increase the absorption of carbon dioxide.

It was reported that, when the centrifugation method is used, the harvesting cost accounts for about 20-30% of the total cost of the microalgae process, even though it depends on the kind of microalgae, cell concentration and a culture method. The harvesting cost is generally calculated by averaging the costs incurred in the process of separating microalgae from the culture medium using continuous centrifugation as opposed to batchwise centrifugation. In other words, continuous centrifugation consumes a large amount of energy, because the concentration of microalgae in the culture medium is low. It was reported that energy required to separate microalgae from a culture medium containing 0.04-4% (on a dry weight basis) microalgae by centrifugation reaches 1.3 kWh/m$^3$ and that energy of about 8 kWh/m$^3$ is consumed to make a dry weight of 22% by centrifugation.

When microalgae are harvested using a membrane filter, power required to obtain a harvesting efficiency of 70% is no more than 0.25 kWh/m$^3$, and thus the use of centrifugation in the production of biodiesel has low cost effectiveness.

Recently, technology of floating the microalgae of the culture medium by applying a vacuum was also developed. It was reported that, when the flotation method that uses a vacuum is used, energy required to harvest microalgae is 0.2 kWh/kg DW, which is 10-100 times lower than those of the existing flocculation method and centrifugation method. However, the flotation method has a problem in that the initial capital investment is higher than those of other methods.

In addition, in patent documents 1 to 1 3, the culture, flocculation and recovery of microalgae are performed in a single reactor, and thus microalgae are harvested in large amounts. However, the above patent documents encounter problems in that the culture and harvesting of microalgae are time-consuming and the concentration of microalgae is low.

PRIOR ART LITERATURE

Patent Documents

Patent document 1: Korean Patent Laid-Open Publication No. 10-2005-0081766 entitled "Continuous Photoreactor for Reduction of Carbon Dioxide and Mass Production of Microalgae"

Patent document 2: Korean Patent Laid-Open Publication No. 10-2011-0094830 entitled "Photobioreactor for High-Density Culture of Microalgae and Method for Culturing and Harvesting Microalgae Using The Same"

Patent document 3: Korean Patent Laid-Open Publication No. 10-2013-0025742 entitled "Photobioreactor for Culture of Microalgae"

SUMMARY OF THE INVENTION

Accordingly, the present invention has been made in order to solve the above-described problems occurring in the art, and it is an object of the present invention to provide a method for photoculturing and harvesting microalgae, which uses a light-emitting diode (LED) having a higher light efficiency than a fluorescent lamp used in the prior art to thereby increase the efficiency with which microalgae are cultured, does not require a cooling system because the generation of heat from the LED is insignificant compared to the fluorescent lamp used in the prior art, and does not need to use a separate filter for removing harmful wavelengths because the LED does not emit light having wavelengths unnecessary for culture.

Another object of the present invention is to provide a method for photoculturing and harvesting microalgae, in which cultured microalgae are harvested using a natural polymer flocculant and air microbubbles, unlike the prior art method of harvesting microalgae using a centrifuge and chemical flocculants, so that the operating cost and the like are reduced, making the method cost-effective, and harvested microalgae contain no chemical substance so that the use thereof is not limited.

Still another object of the present invention is to provide a method for photoculturing and harvesting microalgae, in which a reactor for culturing microalgae and a flocculation/recover tank for flocculating and recovering cultured microalgae are used separately, unlike the prior art in which the culture, flocculation and recovery of microalgae are performed in a single reactor, and microalgae are recovered after harvesting a portion of a microalgae culture at the peak of the growth curve of microalgae, so that the maximum concentration of microalgae can be produced again within a short time, even though the amount of microalgae harvested is small.

To accomplish the above objects, the present invention provides a method for photoculturing and harvesting microalgae, the method comprising:

a step (S100) of introducing a microalgae culture into a reactor, and irradiating the microalgae culture with light emitted from a light source to photoculture microalgae;

a step (S200) of primarily harvesting a portion of the microalgae culture resulting from step S100 into a flocculation/recovery tank;

a step (S300) of introducing air microbubbles together with a natural polymer flocculant into the microalgae culture resulting from step S200 to flocculate and float the microalgae; and a step (S400) of secondarily harvesting the flocculated and floated microalgae resulting from step S300.

Herein, the light source is preferably a light emitting diode (LED).

In addition, the LED preferably includes one or more of a red LED having a wavelength of 650-700 nm and a blue LED or white LED having a wavelength of 400-500 nm and radiates light at an illumination intensity of 1700-9000 Lux and a light intensity of 50-165 μmol/m$^2$/s.

Meanwhile, step S200 is preferably performed by harvesting 10-50 vol % of the microalgae culture resulting from step S100 into the flocculation/recovery tank.

In addition, the natural polymer flocculant is preferably introduced in an amount of 0.05-0.5 parts by weight based on 100 parts by weight of the microalgae culture.

Herein, the natural polymer flocculant is preferably aluminum chloride hexahydrate (AlCl$_3$.6H$_2$O) or polyglutamic acid (PGα21Ca).

In addition, the air microbubbles preferably have a size of 2-20 μm and are introduced at a rate of 0.30-0.40 vvm for 5-15 minutes.

BRIEF DESCRIPTION OF THE DRAWINGS

The above and other objects, features and advantages of the present invention will be apparent from the following detailed description of the preferred embodiments of the invention when taken in conjunction with the accompanying drawings, in which.

EXPLANATION ON SYMBOLS

S100: photoculture microalgae

S200: primarily harvest microalgae

S300: flocculate and float microalgae
S400: secondarily harvest microalgae

DETAILED DESCRIPTION OF THE PREFERRED EMBODIMENTS

Hereinafter, the method for photoculturing and harvesting microalgae according to the present invention will be described in detail.

Figure 1:
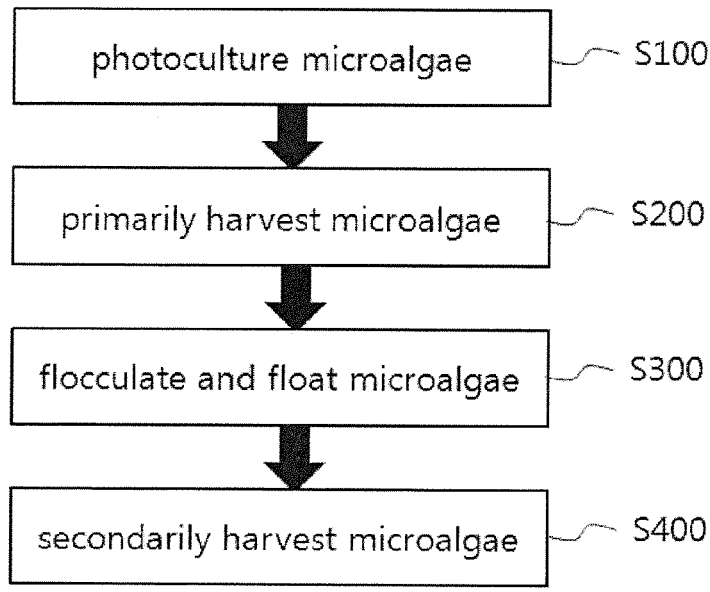
FIG. 1 is a flowchart showing a method for photoculturing and harvesting microalgae according to an embodiment of the present invention.
Figure 2:
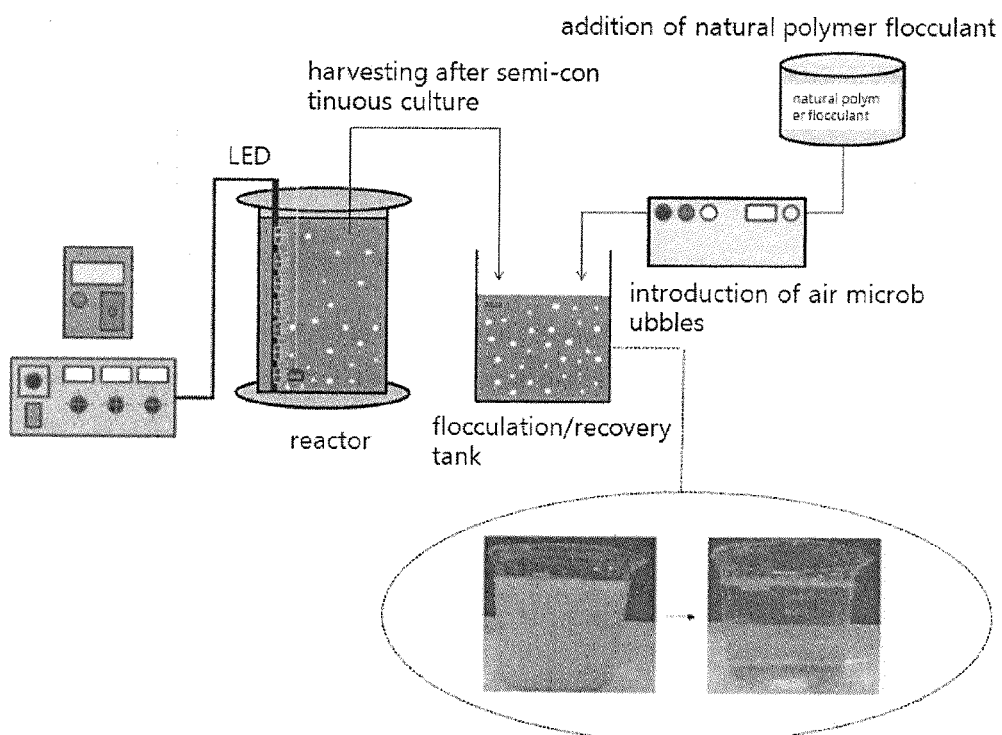
FIG. 2 is a schematic view showing a method for photoculturing and harvesting microalgae according to an embodiment of the present invention.

As shown in FIGS. 1 and 2, the method for photoculturing and harvesting microalgae according to the present invention comprises the steps of: (S100) photoculturing microalgae; (S200) primarily harvesting microalgae; (S300) flocculating and floating microalgae; and (S400) secondarily harvesting microalgae.

Step (S100) of photoculturing microalgae is a step of introducing a microalgae culture into a reactor, and irradiating the microalgae culture with light emitted from a light source to photoculture microalgae. As the light source, LED (light emitting diode) is used.

Specifically, in the present invention, a light-emitting diode (LED) having a higher light efficiency than a fluorescent lamp is used, and thus the efficiency with which microalgae are cultured can be increased. In addition, a cooling system is not required because the generation of heat from the LED is insignificant compared to the fluorescent lamp used in the prior art. Also, a separate filter for removing harmful wavelengths does not need to be used, because the LED does not emit light having wavelengths unnecessary for culture.

Herein, the LED comprises one or more of a red LED having a wavelength of 650-700 nm and a blue LED or white LED having a wavelength of 400-500 nm and radiates light at an illumination intensity of 1700-9000 Lux and a light intensity of 50-165 $\mu mol/m^2/s$.

If the wavelength, illumination intensity and light intensity of the LED are lower than the lower limits of the above ranges, the specific growth rate and the maximum cell concentration can be reduced, and if these values are higher than the upper limits of the above ranges, the method can be cost-ineffective.

Meanwhile, the microalgae culture is a solution obtained by culturing microalgae in a medium and diluting the culture. In the present invention, various microalgae may be used, including *Chlorella* sp., *Nannochloropsis* sp., *Botryococcus* sp., *Scenedesmus* sp. and *Spirulina* sp., and various media can be used.

Step (S200) is a step of primarily harvesting a portion of the microalgae culture resulting from step S100 into a flocculation/recovery tank. In this step, 10-50 vol % of the microalgae culture resulting from step S100 is harvested into the flocculation/recovery tank.

Specifically, a portion of a microalgae culture is harvested at the peak of the growth curve of microalgae, so that the maximum concentration of microalgae can be cultured and produced again within a short time, even though the amount of microalgae harvested is small.

If the amount of microalgae harvested in step S200 is out of the above range, the effect of culturing microalgae can be insufficient.

The growth curve of microalgae can vary depending on the kind of microalgae, operating conditions and environment and is not specifically limited.

In the present invention, the growth curve of microalgae is determined according to the conditions (kind of microalgae, operating conditions and environment), after which the time point at which microalgae are primarily harvested is determined.

Step (S300) of flocculating and floating microalgae is a step of introducing air microbubbles together with a natural polymer flocculant into the microalgae culture resulting from step S200 to flocculate and float the microalgae. In this step, the natural polymer flocculant is added in an amount of 0.05-0.5 parts by weight based on 100 parts by weight of the microalgae culture resulting from step S200, and at the same time, air microbubbles having a size of 2-20 µm are introduced at a rate of 0.30-0.40 vvm for 5-15 minutes, whereby the flocculated microalgae are adsorbed onto the bubbles and floated. In other words, the operating cost for harvesting microalgae is reduced, making the method cost-effective, and the harvested microalgae contain no chemical substance, and thus the use thereof is not limited.

Herein, the natural polymer flocculant that is used in the present invention may be aluminum chloride hexahydrate ($AlCl_3 \cdot 6H_2O$) or polyglutamic acid (PGα21Ca). If the natural polymer flocculant is added in an amount of less than 0.05 parts by weight, the effect of flocculating microalgae will be insufficient, and if it is introduced in an amount of more than 0.5 parts by weight, floatation of the microalgae by the air microbubbles in secondary harvesting step (S400) as described below will be insufficient.

In addition, if the size, injection rate and injection time of the air microbubbles are out of the above ranges, the flocculated microalgae will not be sufficiently floated.

Meanwhile, the air microbubbles can contain carbon dioxide.

In secondary harvesting step (S400), the microalgae, flocculated by the natural polymer flocculant in step S300 and floated by the air microbubbles, are harvested using a conventional harvesting device.

Hereinafter, the present invention will be described in further detail with reference to examples, but the scope of the present invention is not limited to these examples.

1. Photoculturing and Harvesting of Microalgae

PREPARATION EXAMPLE 1

Microalgae Culture

A microalgae strain used in the present invention was *Chlorella* sp. FC-21 obtained from the Korea Marine Microalgae Culture Center (KMMCC), and a medium used in the present invention was prepared by sterilizing a JM medium (Jaworski's Medium, Thompson et al., 1988) having the composition shown in Table 1 below at 121° C. for 15 minutes. Herein, the maximum cell concentration was $2 \times 10^7$ cells/mL.

TABLE 1

| Composition | (unit: mg/L deionized water) Content |
|---|---|
| $Ca(NO_3)_2 \cdot 4H_2O$ | 20 |
| $KH_2PO_4$ | 12.4 |
| $MgSO_4 \cdot 7H_2O$ | 50 |
| $NaHCO_3$ | 15.9 |
| $Na_2HPO_4 \cdot 12H_2O$ | 36 |
| $NaNO_3$ | 80 |
| EDTA FeNa | 2.25 |
| $EDTANa_2$ | 2.25 |
| $H_3BO_3$ | 2.48 |
| $MnCl_2 \cdot 4H_2O$ | 1.39 |
| $(NH_4)_6Mo_7O_{24} \cdot 4H_2O$ | 1.00 |
| cyanobalamin | 0.04 |
| thiamine HCl | 0.04 |
| biotin | 0.04 |

EXAMPLE 1

The microalgae culture prepared in Preparation Example 1 was introduced into a reactor and irradiated with a red LED having a wavelength of 650 nm at a lamination intensity of 1700 Lux and a light intensity of 50 µmol/m²/s to culture the microalgae. Then, 50 vol % of the microalgae culture was primarily harvested into a flocculation/recovery tank. Then, 0.05 parts by weight of polyglutamic acid (PGα21Ca) was added to the harvested microalgae culture while air microbubbles having a size of 2 µm were introduced at a rate of 0.40 vvm for 5 minutes, and the flocculated and floated microalgae were secondarily harvested.

EXAMPLE 2

The microalgae culture prepared in Preparation Example 1 was introduced into a reactor and irradiated with a white LED having a wavelength of 650 nm at a lamination intensity of 9,000 Lux and a light intensity of 165 µmol/m²/s to culture the microalgae. Then, 10 vol % of the microalgae culture was primarily harvested into a flocculation/recovery tank. Then, 0.5 parts by weight of aluminum chloride hexahydrate ($AlCl_3 \cdot 6H_2O$) was added to the harvested microalgae culture while air microbubbles having a size of 20 µm were introduced at a rate of 0.30 vvm for 15 minutes, and the flocculated and floated microalgae were secondarily harvested.

COMPARATIVE EXAMPLE 1

The microalgae culture prepared in Preparation Example was introduced into a reactor and irradiated with a fluorescent lamp at the same light intensity as that the LED of Example 1, and the microalgae were incubated. Then, 0.5 parts by weight of $CaCl_2$ was added thereto, after which the microalgae were harvested using a centrifuge.

2. Evaluation of Final Concentration of Microalgae

The final concentrations of the microalgae harvested according to the methods of Examples 1 and 2 and Comparative Example 1 was measured by a direct microscopic method, and the results of the measurement are shown in Table 2 below.

TABLE 2

| | Operation time | Final concentration |
|---|---|---|
| Example 1 | 6 days | $2*10^8$ cells/mL |
| Example 2 | 3 days (semi-continuous culture) | $7*10^8$ cells/mL |
| Comparative Example 1 | 6 days (irradiation with fluorescent lamp) | $1*10^7$ cells/mL |

As can be seen in Table 2 above, the final concentrations of the microalgae harvested according to Examples 1 and 2 of the present invention were higher than that of Comparative Example 1.

As described above, in technical terms, the present invention provides a technical basis on which LED can be used for the culture of microalgae, and thus significantly high productivity and cost effectiveness compared to conventional methods for culture of microalgae. Also, the present invention makes it possible to increase the productivity of the harvesting process and reduce the cost, because the harvesting cost in an actual biodiesel or bioethanol production process accounts for 20% of the total process cost. Moreover, a combination of semi-continuous culture and a microalgae harvesting system is used so that the continuity of the overall process can be maintained, and an automatic process is introduced so that the management cost can be reduced.

In environmental terms, the culture of microalgae can greatly contribute to sewage/wastewater treatment and bioremediation for removing contaminants from the sea and freshwater. In order to solve a problem of the eutrophicat ion of lakes an marshes, the concentration of nutrient salts in effluent water should be significantly reduced, and for this purpose, the advanced treatment of sewage/wastewater is necessary. In the advance treatment, the efficiency with which nitrogen or phosphorus is removed from effluent water can be increased using microalgae having high ability to accumulate nitrogen and phosphorus. In a typical example of wastewater treatment using microalgae, when microalgae are cultured in an. oxidation pond filled with waseaer, a combination of microalgae, bacteria, animal plankton and residue, called "albazod", is formed. When the present invention is applied to this treatment in the oxidation pond, it can greatly contribute to water purification by increasing the treatment efficiency. Also, it is known that the microalgae culture system can be applied to treat heavy metals in wastewater and that some marine or fresh-water microalgae have an excellent function of selectively absorbing heavy metals and accumulating the absorbed heavy metals in the body. Thus, the present invention can provide a new method capable of removing contaminants.

In economic and industrial terms, industrially important useful substances can be produced by culture of microalgae, and biomass and industrially useful substances can be used in various applications, including health supplement foods, feed, cosmetic products, raw materials for developing new drugs, transportation fuels or energy, etc. With the development of the marine products artificial cultivation industry, the demand for microalgae as fish feed is increasing. Also, freshwater chlorella is used as feed for Rotifer, contains large amounts of minerals, vitamins and essential amino acids and has various physiological activities, and thus it can be used as a feed additive and a food additive and in cosmetic produces and medical drugs. LED-marine convergence technology can create new markets in the marine products industry, the marine bio-industry, marine environmental control and the like and can play an important role in the rehabilitation and growth of the related industries, and thus it can contribute to increasing the added value of ;he marine industry and to the rehabilitation of the marine industry. The LED industry is expected to have a worldwide market size of 100 billion dollars in the year 2015 and an annual mean growth rate of 41%. The present invention can expand the application of LED and contribute to the market formation and growth of the LED industry. In Korea, the LED illumination market is growing rapidly in the year 2012, and the LED-agricultural/biological field and the LED-marine field will enter the growth phase in the year 2015. Thus, the present invention can be used as a leading invention according to this tendency.

While the preferred embodiments of the method for photoculturing and harvesting microalgae according to the present invention has been shown and described with reference to the accompanying drawings, they are merely illustrative embodiments, and the invention is not limited to these embodiments. It is to be understood by a person having an ordinary skill in the art that various equivalent modifications and variations of the embodiments can be made without departing from the spirit and scope of the present invention. Therefore, various embodiments of the present invention are merely for reference in defining the scope of the invention, and the true technical scope of the present invention should be defined by the technical spirit of the appended claims.

What is claimed is:

1. A method for photoculturing and harvesting microalgae, the method comprising:
   a step a) of introducing a microalgae culture into a reactor, and irradiating the microalgae culture with light emitted from a light source to photoculture microalgae;
   a step b) of primarily harvesting a portion of the microalgae culture resulting from step a) into a flocculation/recovery tank;
   a step c) of introducing air microbubbles together with a natural polymer flocculant into the microalgae culture resulting from step b) to flocculate and float the microalgae; and
   a step d) of secondarily harvesting the flocculated and floated microalgae resulting from step c),
   wherein the light source is a light emitting diode (LED),
   wherein the LED comprises one or more of a red LED having a wavelength of 650-700 nm and a blue LED or white LED having a wavelength of 400-500 nm, and radiates light at an illumination intensity of 1700-9000 Lux and a light intensity of 50-165 $\mu mol/m^2/s$,
   wherein step b) is performed by harvesting 10-50 vol % of the microalgae culture resulting from step a) into the flocculation/recovery tank,
   wherein the natural polymer flocculant is added in an amount of 0.05-0.5 parts by weight based on 100 parts by weight of the microalgae culture resulting from b),
   wherein the natural polymer flocculant is aluminum Chloride hexahydrate ($AlCl_3.6H_2O$) or polyglutamic acid (Pgα21Ca), and
   wherein the air microbubbles have a size of 2-20 μm and are introduced at a rate of 0.30-0.40 vvm for 5-15 minutes.

* * * * *